United States Patent [19]

Piet et al.

[11] 4,108,509

[45] Aug. 22, 1978

[54] CONTROLLED ENVIRONMENT WORK ENCLOSURE

[75] Inventors: Meyer Piet, Arcadia; Dean Gaylord Giles, Valinda, both of Calif.

[73] Assignee: Futurecraft Corporation, City of Industry, Calif.

[21] Appl. No.: 779,013

[22] Filed: Mar. 18, 1977

[51] Int. Cl.² .......................... B01D 53/34; B01L 1/00
[52] U.S. Cl. ........................................ 312/1; 32/40 A
[58] Field of Search ................... 312/1, 2; 128/1 B; 32/40 A; 23/259

[56] References Cited

U.S. PATENT DOCUMENTS

| | | | |
|---|---|---|---|
| 2,786,740 | 3/1957 | Taylor | 312/1 |
| 3,084,684 | 4/1963 | Saunders | 312/1 |
| 3,536,370 | 10/1970 | Evans et al. | 312/1 |
| 3,971,644 | 7/1976 | Sugarman | 312/1 |

*Primary Examiner*—Casmir A. Nunberg
*Attorney, Agent, or Firm*—James E. Brunton

[57] ABSTRACT

An improved controlled atmosphere work enclosure for use in handling hazardous materials such as mercury and mercury alloys. The work enclosure comprises a hollow housing defining a work space within which an amalgamator unit, work platform, or the like can be mounted. Replaceable flexible plastic or rubber gloves are sealably affixed to glove rings mounted on the front of the unit to permit convenient working access to the amalgamator or work platform. Filtered air inlets are provided at each side of the work enclosure and a filtered air outlet is installed in the rear wall thereof above the work area. A fan unit is mounted exteriorly of the enclosure proximate the air outlet to maintain subatmospheric pressure within the enclosure and to cause air to be continuously drawn inwardly through the air inlets, through the work area and upwardly and rearwardly toward the filtered outlet. Use of the enclosure permits hazardous materials to be safely and expeditiously handled and stored without fear of environmental contamination.

8 Claims, 6 Drawing Figures

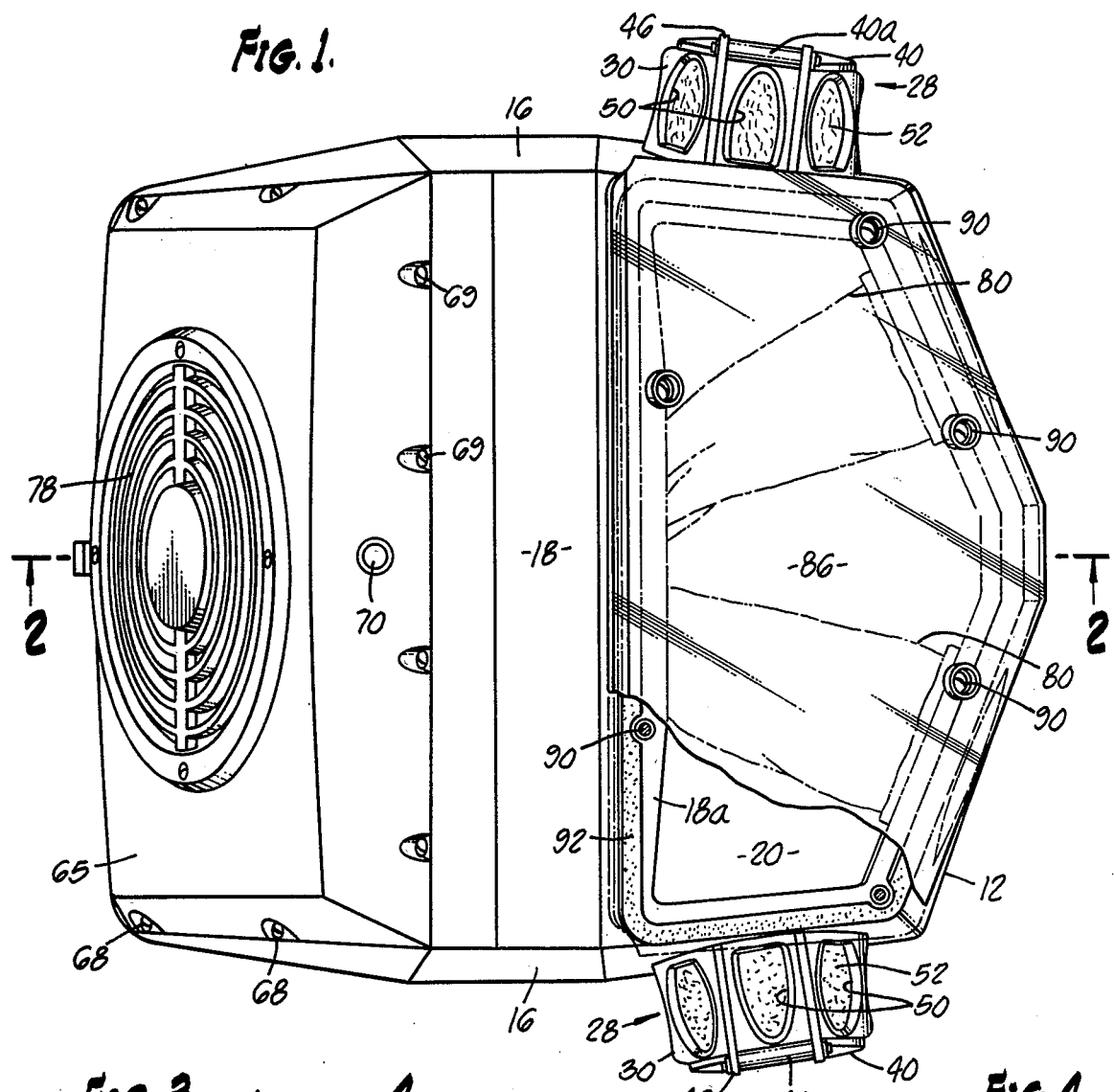

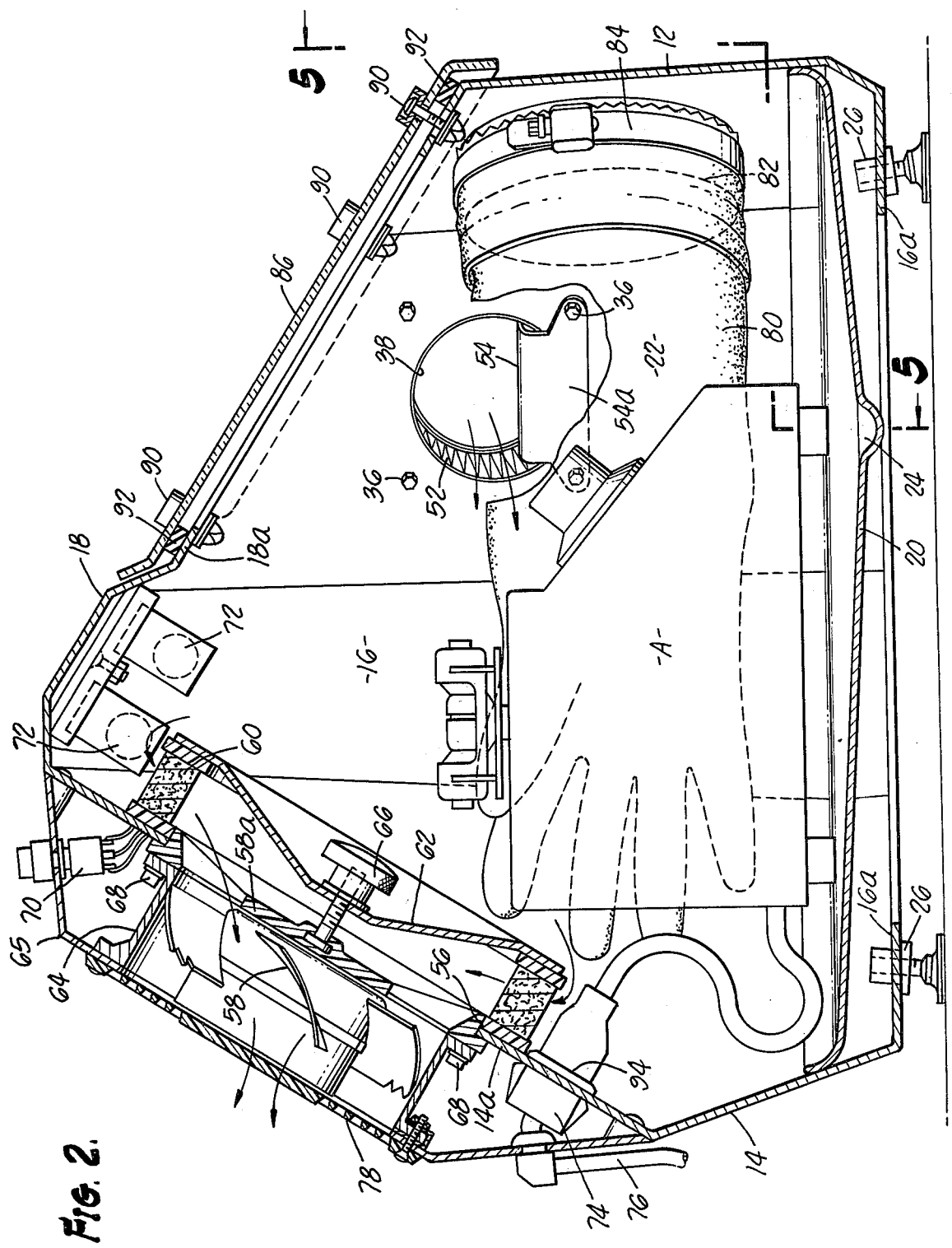

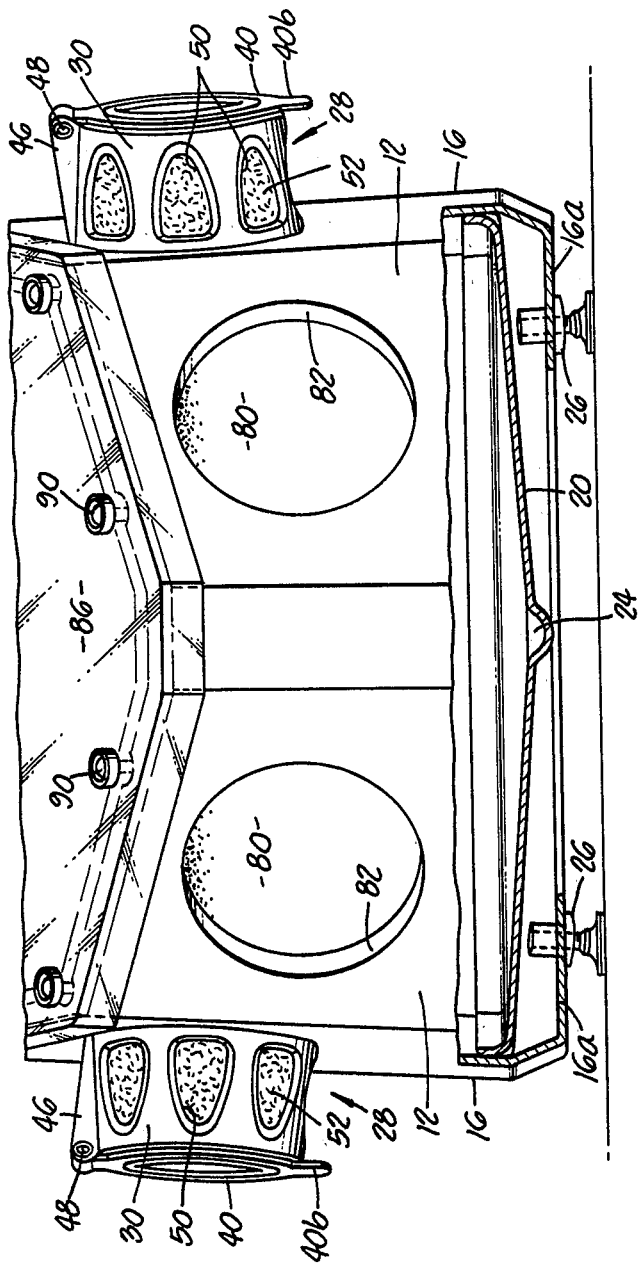
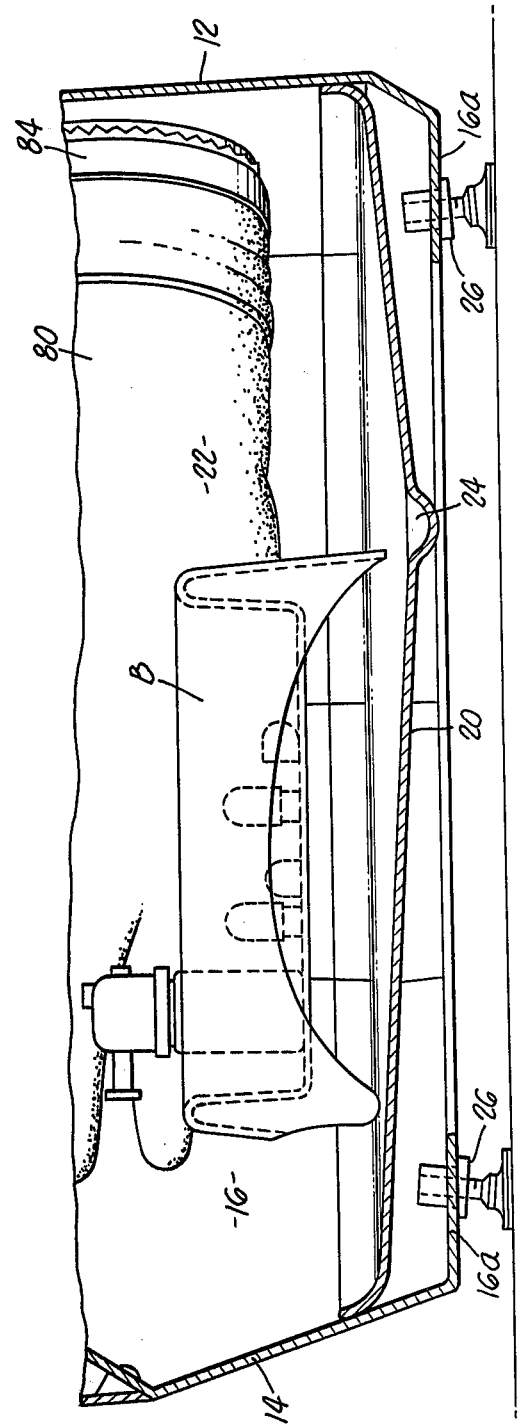

CONTROLLED ENVIRONMENT WORK ENCLOSURE

BACKGROUND OF THE INVENTION

1. Field of the Invention

The present invention relates generally to enclosures for handling hazardous materials and, more particularly, to an improved controlled atmosphere work enclosure adapted to be used in dental operatories for mixing, mulling, cutting, and storing amalgam.

2. Discussion of the Prior Art

Of major national concern are health hazards resulting from environmental pollution. Among the more deadly sources of pollution are the heavy metals, and of these mercury is one of the most hazardous and difficult to control.

Of particular concern are the hazards presented through careless handling of mercury in the dental office and dental operatory. In fact, the abnormally high rate of suicide among dentists is believed by many experts to be directly linked to Mercury poisoning. Since the dental profession in the United States uses in excess of 200,000 pounds of mercury per year, or about 4 percent of the total amount used in the United States, a significant threat is presented, not only to the health of the dentist, but to his auxiliary personnel as well.

Environmental contamination through the use of mercury in dental operatories originates primarily from mercury spills and leakage or failure of mercury-containing capsules used in the trituration process. Additionally, mere excitation of any mercury contamination which may reside on the surfaces of the capsules or upon tools and equipment used in the operatory causes the mercury to vaporize and immediately spread throughout the adjacent areas. Also contributing to the inordinately high level of mercury contamination found in dental offices and operatories is simple carelessness by the dentist and his assistants in the open air mulling, amalgam cutting, and mercury storage.

Recent studies show that seven out of ten dental operatories tested showed mercury vapor levels significantly above the threshhold limit of 50 micrograms per cubic meter. These studies further revealed that urinary mercury levels tended to parallel vapor exposure and that the urinary level of the average dentist was twice that of the accepted normal level (20.40 micrograms Hg/24 hrs. vs. 9.95 micrograms Hg/24 hrs.).

One of the detrimental effects of the excessive mercury exposure is acute anxiety. This factor is believed linked with mental illness and it has recently been established through statistical studies that dentists take their own lives twice as often as the general population.

Although mercury contamination poses a particular threat in dental offices and laboratories, the problem is by no means limited to such operatories. Wherever mercury is handled, be it in hospitals, scientific laboratories, or industrial plants, mercury contamination presents a significant health hazard. In hospitals and scientific laboratories, the mercury hazard arises from many sources, including the use of several pieces of apparatus such as the Coulter counter, the Van Slyke apparatus, Miller-Abbot, and Cantor tubes.

In recent years, various approaches have been suggested to control mercury contamination in dental operatories, hospitals, and laboratories. For example, several types of mercury vapor sensing devices have been developed to monitor mercury vapor levels. Similarly, a wide variety of filtered room exhaust units have been proposed to control atmospheric contamination. Little has been done, however, to prevent the contamination from occurring in the first place. Although expedients such as prepackaged amalgam capsule systems, wherein the mercury and alloy are stored and mixed in cartridges, have come into relatively wide use, such systems have exhibited several disadvantages. In addition to the propensity of the cartridges to leak during storage and to break during mixing operations, their handling and disposal after the amalgam is mixed contributes to environmental contamination.

One of the most successful systems developed for use in handling hazardous materials is disclosed in our copending application Ser. No. 672,570. The apparatus of the present invention comprises an improvement of the apparatus disclosed in said application. As will be better understood from the discussion which follows, the work station of the present invention provides a totally enclosed, controlled environment workspace wherein various mercury handling operations such as mixing, mulling, and amalgam cutting, can be accomplished in absolute safety with no fear of personnel or atmospheric contamination. Mercury spills are completely contained within the unit and because of the unique design of the floor of the unit the spilled mercury is collected in a small reservoir or sump from which it can be readily and safely collected, thereby precluding any possible spread of contamination. All mercury handling operations are conducted through rubber gloves which are sealably connected to the unit so as to prevent personnel contamination through direct handling of the mercury. The relative positions of the air inlet and air outlet parts of the apparatus, the novel design of the filters, and the position of the fan unit provide a unique air circulation pattern within the enclosure thereby enabling highly effective control of both vaporous and particulate mercury within the system. In the apparatus of the present invention, unlike that disclosed in our copending application, the air is drawn inwardly through the air inlets, through the work space and then rearwardly and upwardly toward the air outlet. For certain applications this arrangement has proven superior in controlling particulate contamination, particularly when mercury is being handled within the unit. Tests have shown that the mercury level within the air stream emitted from the unit of the present invention during mercury handling operations is consistently less than one half part per million.

The work enclosure of the present invention, when used in the dental operatory, is large enough to accommodate work tables of ample size for loading, mixing, cutting, and storing mercury and mercury alloys. Additionally, the work enclosure is designed to readily accommodate amalgamators of the latest design.

Regular use of the work enclosure of the invention by the dentist and his assistants for all amalgam work virtually eliminates the threat of environmental contamination of the operatory with mercury.

When it is desired to use the work station of the invention in hospitals or scientific laboratories, it is to be appreciated that appropriate internal modifications can readily be made to accommodate numerous types of tools and instruments. Additionally, by use of special filters, the enclosure can readily be adapted to safely handle hazardous materials other than mercury such as toxic chemicals, radioactive materials, and the like.

SUMMARY OF THE INVENTION

It is an object of the present invention to provide an improved compact, self-contained, controlled environment work station in which hazardous materials such as heavy metals, radioactive isotopes, toxic chemicals, and the like, can be safely handled without fear of contamination of the technician, the surrounding atmosphere, or the operational area in which the work enclosure is used.

More particularly, it is an object of the present invention to provide a controlled environment work station adapted for use by the dental profession for mixing, mulling, cutting, and storage of amalgam.

It is another object of the invention to provide a work enclosure of the aforementioned character in which, during use, there is maintained within the enclosure a subatmospheric pressure and in which, due to the relative size and position of the air inlet and outlet ports, filtered air is continuously drawn inwardly and then moved uniformly through the work enclosure and outwardly through a filter which is strategically located rearwardly and above the work area.

It is another object of the invention to provide a work enclosure as described in the preceding paragraph in which specially designed filter mediums are operably associated with both the air inlets and the air outlets of the enclosure to preclude the escape of vaporous or particulate materials and in which an exhaust fan is mounted exteriorly of the work enclosure in operable association with the filtered air outlet.

It is still another object of the invention to provide a work enclosure of the class described which is particularly adapted for dental work and can accommodate the dentist's amalgamator and associated amalgam handling equipment.

It is a further object of the invention to provide a work station as described in the previous paragraph in which the work chamber is sufficiently large to conveniently accommodate the amalgamator and to permit the dentist and his assistants to proportion, load, mix, store and dispense amalgam in the normal manner, but without fear of personnel or environmental mercury contamination.

It is another object of the invention to provide a work enclosure of the type described in which the floor of the unit is uniquely configured so as to slope in all directions toward a low point defining a reservoir or sump adapted to collect and hold any mercury which may be accidently spilled during the mercury handling operation.

It is another object of the invention to provide a work enclosure as described in which the fan unit, the light starters, and all other heat generating equipment is mounted exteriorly of the unit to minimize vaporization of the mercury being handled within the enclosure.

It is still another object of the invention to provide a work enclosure of the class described in which there is included a novel pass-through arrangement to permit safe introduction and withdrawal of material from the enclosure during operation without risk of contaminating the environment or the surrounding work area. The novel air flow within the unit insures effective removal of all mercury contamination from objects placed within the pass-through so as to prevent spread of contamination.

It is a further object of the invention to provide a work enclosure as described in the preceding paragraphs which is well lighted, includes a strategically located removable viewing panel and in which convenient access to the working area is accomplished through flexible plastic or rubber gloves which are removably affixed to glove rings mounted on the front panel of the unit. The gloves provided are of ample length to reach all areas of the chamber comfortably, are very pliable, and assure complete freedom of movement by the technician.

It is yet another object to provide a work enclosure as previously described which is attractive, sturdy, highly reliable in use, requires minimum maintenance, provides maximum safety to the user, and yet is of a simple design which can be readily and inexpensively manufactured.

These and other objects of the invention are achieved by a controlled environment work enclosure comprising interconnected front, back, side, bottom, and top walls defining a work space; at least one air inlet provided in the side walls of the housing; an air outlet provided in the back wall of the housing above the work space; suction means for maintaining subatmospheric pressure in the work enclosure and for drawing a stream of air inwardly through the air inlets, through the work space, and upwardly and rearwardly toward the air outlet; and filter means interposed in the stream of air between the suction means and the work space for preventing vapors and particulate materials from escaping from the work enclosure through the air outlet.

BRIEF DESCRIPTION OF THE DRAWINGS

FIG. 1 is a top plan view of the improved controlled environment work enclosure of the present invention.

FIG. 2 is a side elevational cross sectional view taken along lines 2—2 of FIG. 1 showing an amalgamator in position within the work enclosure.

FIG. 3 is a fragmentary side view of the combined air inlet and pass-through part of the work enclosure of the invention.

FIG. 4 is a cross sectional view of the part taken along lines 4—4 of FIG. 3.

FIG. 5 is a front elevation taken along lines 5—5 of FIG. 2 showing the sloping configuration of the floor of the work enclosure.

FIG. 6 is a partial view similar to FIG. 2 showing a work table rather than an amalgamator positioned within the work enclosure.

PREFERRED EMBODIMENT OF THE INVENTION

Referring to the drawings, and particularly to FIGS. 1 and 2, the controlled environment work enclosure of the present invention comprises interconnected front, back, side, top, and bottom walls 12, 14, 16, 18, and 20 respectively, defining a closed chamber or workspace generally designated by the numeral 22. Provided in bottom wall 20 is a material collection reservoir or sump 24 which is disposed substantially centrally of the work space. As can be seen by also referring to FIG. 5, bottom wall 20 is specially configured so as to slope downwardly from the front, back, and side walls of the enclosure toward sump 24. Sump 24 is an important feature of the present invention. When the enclosure is used for mercury handling, the spilled mercury will flow to the sump where it can be readily and safely recovered.

The enclosure walls may be constructed from a wide variety of materials including sheet metal, plastic, fiber composites, and the like, which are suitably interconnected to form a hollow housing by the use of fasteners, bonding materials, or by welding.

Affixed to inturned flanges 16a provided at the bottom of side walls 16 are front and rear supporting legs 26 (FIG. 2) which are readily adjustable to insure that the apparatus is firmly supported on a work surface. The work enclosure is of sturdy construction so that when the unit is used in a dental office it will safely support an amalgamator machine, generally designated by the letter "A" or a replaceable worktable generally designated by the letter "B" (FIG. 6). The amalgamator is of standard design and may rest on the subfloor or be attached thereto either by clamps, by bonding, or by other suitable fasteners. As indicated in the drawings, the apparatus is sufficiently large to accommodate placement of the amalgamator, as well as various tools and equipment used by the dentist to proportion, load, mix, and store amalgam. The design of worktable B varies depending upon the work being performed within the enclosure. As shown in FIG. 6, the worktable is adapted to hold mercury capsules and mercury mixing, cutting, and mulling tools.

Another important feature of the work enclosure of the present invention is the unique air circulation system adapted to provide a continuous and uniform flow of air through the work space during operation of the device. As illustrated by the directional arrows of FIG. 2, air enters the enclosure through a pair of spaced apart air inlet assemblies 28 (FIG. 1) carried by side walls 16 of the housing. In this form of the invention, assemblies 28 comprise pass-through means for permitting the introduction and removal of articles from the work enclosure.

As best seen in FIGS. 1 and 4, assemblies 28 each comprise a generally tubular shaped element 30 having inturned inner and outer flanges 32 and 34 respectively (FIG. 4). Elements 30 are affixed, as by threaded fasteners 36, to side walls 16 in register with generally circular openings 38 provided therein. The outboard ends of elements 30 are closed by a hingeably mounted closure member or door 40. Carried in grooves 42 formed on the inner walls near the outer periphery of doors 40 are gasket members 44 formed of a yieldably, resilient rubber or neoprene material. When the doors are closed, the gasket members 44 engage the outer surface of flange 34 of element 30 so as to prevent the flow of air between the door and element 30.

Referring particularly to FIG. 3, formed at the upper edge of each door 40 is an outwardly extending earlike segment 40a which is closely receivable between spaced apart flanges 46 formed near the top of each element 30. Flanges 46, as well as segments 40a, are bored to receive a hinge pin 48 which forms the axis for swingable movement of the doors relative to elements 30. Opposite segments 40a formed on doors 40 are second earlike segments 40b which may be conveniently grasped by the operator to open and close the doors 40.

A unique feature of this embodiment of the invention is that the pass-through means also form the air inlets of the apparatus. As shown in FIGS. 1, 3, and 4, elements 30 are provided with a plurality of openings 50 which, in a manner presently to be described, permit air to flow into the apparatus through the openings 38 formed in the housing walls 16. Removably mounted interiorly of each element 30 is a first or inlet filter means shown here in the form of annular shaped fibrous dust filters 52. Filters 52 function to remove dust particles or other particulate materials from the room air as it is drawn into the apparatus through apertures 50. Filters 52 also perform the important function of prohibiting migration of mercury vapors through the air inlets to the exterior of the work enclosure when the unit is in a nonoperating, static mode.

Also mounted within each element 30 is a shelf or table 54 (FIG. 4) upon which articles may be placed during work operations. Shelves 54 include downwardly extending flanges 54a which are adapted to receive fasteners 36 so that the shelves can be securely connected in the manner shown to walls 16 of the work enclosure. As shown in FIG. 4, the shelves are also provided with a plurality of perforations 54b and are located within tubular elements 30 in the path of the stream of air being drawn inwardly into the work enclosure. With this arrangement, any vapor or particulate material on the surfaces of an article placed on the shelves will continuously be urged inwardly of the enclosure.

To create the desired air flow pattern within the work enclosure, which is critical to effective contamination control, there is provided suction means for drawing air into the enclosure through filters 52 and thence uniformly through the enclosure work space. The air is then urged away from the operator toward an air outlet 56 which is provided in a forwardly sloping portion 14a of back wall 14 of the housing. In the form of the invention shown in the drawings, the suction means comprises a tube-axial fan unit 58 (FIG. 2) mounted exteriorly of back wall portion 14a proximate air outlet 56. As shown by the directional arrows in FIG. 2, fan unit 58 functions to continuously maintain subatmospheric pressure within the work enclosure and cause a smooth continuous flow of air through the air inlets, past shelves 54 and through the work space whereby vaporous or particulate material in the vacinity of the shelves and the work space will be carried rearwardly and upwardly toward a second filter means. The second filter means is provided in this embodiment in the form of an annular-shaped filter 60 which is carried by rear wall portion 14a so that it is disposed between the work space and the fan unit 58. Filter 60 is held against the inner surface of wall 14a in register with air outlet 56 by means of a clamping element 62 which is adjustably interconnected to the central portion 58a of fan unit 58 by means of a threaded connector 66. Fan unit 58, which is carried in a generally cylindrical-shaped fan housing 64, is in turn held against the outer surface of wall 14a in register with outlet 56 by means of fasteners 68. As best seen in FIG. 1, housing 64 is disposed within a cup-shaped cover 65 which is connected to the rear wall of the enclosure by fasteners 69. With the construction shown filter 60 can be replaced by disconnecting connector 66 from a fan support bracket 58a so that clamping element 62 and filter 60 can be moved into the work space of bagging and subsequent removal from the work enclosure.

Also mounted within cover 65 is a starter and switch assembly 70 used for starting fan 58 and florescent lights 72 (FIG. 2). Additionally, an electrical power outlet box 74, which is connected to an external source of electrical power by cables 76, is carried within the cover 65. Experience has shown that by mounting the fan 58 along with the other heat generating elements just mentioned, exteriorly of the work space and venting to atmosphere the heat which they generate, vaporization of temperature sensitive contaminants such as mercury is markedly reduced, thereby significantly enhancing effective contamination control.

The material from which filter 60 is constructed varies depending upon the type of hazardous material being handled within the apparatus. When mercury is being handled, the filter is preferably constructed of a porous graphite material which has been chemically impregnated to absorb and contain mercury both in vapor and particulate form. When radioactive materials are being handled within the enclosure, various types of fibrous materials adapted to capture particulate material may be used in construction of the filter. In any event, filter 60 should be constructed so as to effectively remove the contaminates from the air stream with minimal impedence thereto so as to permit the air to uniformly flow through the filter toward the fan unit 58 for expulsion to room atmosphere. As best seen in FIG. 1, a suitable grille 78 is provided over the fan unit to prevent injury to personnel through contact with the fan blades of the fan.

To enable working access to the interior of the work enclosure, there is provided operator access means shown here in the form of flexible plastic or rubber glove means 80 replaceably affixed to glove rings 82 (FIG. 2) mounted on the front walls of the enclosure. Glove means 80 seal off the entry ports defined by the glove rings and are of sufficient length to enable the technician to comfortably reach all areas of the work enclosure. The glove means are made of a tough but pliable material and assure complete freedom of movement by the technician while working in the enclosure. Glove means 80 are replaceably affixed to glove rings 82 by clamping rings 84 which slip over the glove rings and hold the glove means captive therebetween.

As illustrated in FIGS. 1 and 2, the forward portion 18a of the top wall is provided with a removable viewing panel 86 to enable complete visibility of the amalgamator unit "A" or the worktable "B" shown in FIG. 6. Viewing panel 86 is removably connected to the top wall 18 by quick disconnect fasteners 90 which permit the panel to be readily removed to provide access to the interior of the enclosure. Interposed between panel 86 and top wall 18 is a unique vapor barrier in the form of a density cross-linked, closed cell polyethylene gasket 92 (FIG. 2). During all operations of the system, panel 86 is held tightly against gasket 92 so as to prevent any leakage of contamination between the panel and wall 18.

Operation

With the necessary tools, equipment, supplies and amalgam within the unit, view panel 86 is placed in position and tightly sealed against the gasket member 92 by fasteners 90. Operation of switch 70 then energizes the light and causes fan 58 to begin to operate. Operation of fan 58 causes air to be drawn through openings 50 formed in pass-through element 30, through filters 52, past shelves 54 and finally through air inlet openings 38 into the enclosure. Due to the size and location of the air inlets relative to the air outlet, air will be drawn uniformly through the work space and then rearwardly and upwardly toward filter 60 in the manner indicated by the directional arrows of FIG. 2.

With the air circulating within the work enclosure in the manner described, the operator may safely mix, mull, and cut the amalgam in the normal fashion with no fear of contaminating himself or the enviroment. The amalgamator unit can safely be used in the manner indicated in FIG. 2, or the operator can use the work table as shown in FIG. 6. An electrical receptacle 94 is disposed in the rear wall of the enclosure to provide power to the amalgamator. Materials or tools can be introduced into the enclosure as necessary by means of the pass-through assemblies 28 located at the sides of the apparatus.

At the completion of each amalgam mixing cycle, the capsule is opened, the amalgam poured into an amalgam cup and the cup placed on shelf 54. As previously discussed, the design and location of the shelf is such that any lingering mercury vapor which resulted from the mixing operation, as well as any contaminates on the cup itself, will be carried inwardly of the enclosure by the air stream passing by the shelf.

Because of the unique design of the sloping bottom wall 20 of the work enclosure, any mercury spilled during the mixing, mulling, or cutting operations will immediately flow along the floor toward the sump 24 where it will safely collect for expeditious recovery.

After a predetermined period of operation, perhaps on the order of thirty days, the contaminated outlet filter 60 can be removed and bagged in the manner previously described. Although the smaller inlet filters 50 do not require replacement as frequently as filter 60, when replacement is necessary, such replacement can readily be accomplished by removing the filters from element 30 and replacing them with new filters.

With regard to the actual mixing and manipulation of the amalgam within the enclosure, it is to be appreciated that this can be done in basically the same manner as the work is now being done in dental offices and operatories. For example, with the amalgamator in place in the enclosure, the technician can slip his hands into the glove means and proceed to proportion, measure, and fill the mixing capsules with the alloy pill and mercury. The filled capsule is then positioned within the amalgamator and the amalgamator energized in the normal fashion. As previously described, after mixing is accomplished, the technician opens the capsule, places the amalgam into an appropriate container which may be set on shelf 54 of the pass-through assembly. The technician then removes his hands from the gloves and waits for a few moments to make certain that the air circulation system is properly functioning. With the exhaust fan continuing to run, the technician can then safely open door 40 and remove the amalgam. The unique air flow pattern within the unit allows incoming filtered air to remove any mercury vapor from the amalgam mix so that when the technician opens door 40 to remove the mix there will be no spread of contamination to the work area.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A work enclosure for use in dental operatories to enclose an amalgamator within a controlled atmosphere, comprising:
   (a) interconnected front, back, side, bottom, and top walls defining an enclosed work space, said back wall having a forwardly sloping portion and said top wall having a removable viewing panel provided therein;

(b) a mercury collection sump formed in said bottom wall, said bottom wall being configured to slope downwardly from said front, back, and side walls toward said sump;

(c) glove means replaceably mounted on said front wall for receiving the hands of an operator and permitting manipulation of the amalgamator;

(d) air inlets provided in said side walls of said housing on opposite sides of the work space;

(e) first filter means cooperatively associated with said air inlets for preventing passage therethrough of dust or other particulate material;

(f) an air outlet provided in said forwardly sloping portion of said back wall rearwardly and above the work space;

(g) a motorized suction fan carried by said back wall proximate said air outlet for maintaining subatmospheric pressure in said work enclosure and for drawing a stream of air inwardly from said air inlets through said work space and upwardly and rearwardly toward said air outlet; and (h) second filter means interposed in said stream of air between said work space and said fan for preventing mercury in vapor form contained therein from escaping from said work enclosure through said air outlet.

2. Work enclosure as defined in claim 1 including two spaced apart pass-through means for permitting introduction and withdrawal of articles from the work enclosure, said pass-through means each comprising a generally tubular element affixed at one end to said side wall of said housing in register with an opening formed therein; the opposite end thereof being closed by a hingeably mounted door carried by said tubular element.

3. A work enclosure as defined in claim 2 in which said door when in a closed position is in sealable engagement with sealing means provided in the form of a resilient gasket member disposed intermediate said door and said tubular element, and in which an article supporting shelf is provided interiorly of said tubular member.

4. A work enclosure as defined in claim 3 in which said article supporting shelf is provided with a plurality of perforations, said shelf being located within said tubular element in the path of the stream of air being drawn inwardly of said work enclosure whereby vapor or particulate material on the surfaces of an article placed on said shelf will be urged inwardly of said work enclosure.

5. A work enclosure for use in handling toxic materials in liquid, vapor and particulate form and for containing said materials within a controlled atmosphere, comprising:

(a) interconnected front, back, side, bottom, and top walls defining an enclosed work space, said top wall having a viewing panel provided therein;

(b) glove means replaceably mounted on said front wall for receiving the hands of an operator and permitting manipulation of materials within the work enclosure;

(c) air inlets provided in said housing on opposite sides of the work space;

(d) an air outlet provided in said housing rearwardly and above the work space;

(e) suction means carried by said housing proximate said air outlet for maintaining subatmospheric perssure in said work enclosure and for drawing a stream of air at a substantial velocity inwardly from said air inlets through said work space and upwardly and rearwardly toward said air outlet; and (f) filter means interposed in said stream of air between said work space and said suction means for preventing toxic material in vapor or particulate form contained therein from escaping from said work enclosure through said air outlet.

6. A work enclosure as defined in claim 5 in which said work space is sufficiently large to accomodate a mercury amalgamator therewithin and in which a mercury collection sump is formed in said bottom wall, said bottom wall being configured to slope downwardly from said front, back, and side walls toward said sump.

7. A work enclosure as defined in claim 5 including inlet filter means cooperatively associated with said air inlets for preventing passage therethrough of dust or other particulate material.

8. A work enclosure as defined in claim 7 in which said inlet filter means comprise annular shaped filters carried interiorly of said air inlets.

* * * * *